United States Patent [19]
Grebow et al.

[11] Patent Number: 5,026,825
[45] Date of Patent: Jun. 25, 1991

[54] INTRANASAL CALCITONIN FORMULATIONS

[75] Inventors: Peter E. Grebow, Penllyn; Herschel H. Li, Ambler, both of Pa.; Lewis J. Klunk, Jr., Trumbull, Conn.

[73] Assignee: Rhone-Poulenc Rorer Pharmaceuticals Inc., Fort Washington, Pa.

[21] Appl. No.: 242,000

[22] Filed: Sep. 8, 1988

[51] Int. Cl.$^5$ .................. A61K 37/24; C07K 7/36
[52] U.S. Cl. ..................................... 530/307; 530/324
[58] Field of Search ............... 514/12, 13; 520/324, 520/307

[56] References Cited

U.S. PATENT DOCUMENTS

| | | | |
|---|---|---|---|
| 3,920,814 | 11/1975 | Bocher et al. | 514/40 |
| 4,568,665 | 2/1986 | Mitchell | 514/9 |
| 4,690,952 | 9/1987 | Kagatani et al. | 514/808 |
| 4,692,433 | 9/1987 | Hostetler et al. | 514/12 |
| 4,746,728 | 5/1988 | Orlowski et al. | 530/307 |
| 4,758,550 | 7/1988 | Cardinaux et al. | 514/12 |
| 4,789,667 | 12/1988 | Makino et al. | 514/161 |

Primary Examiner—Lester L. Lee
Assistant Examiner—Avis Davenport
Attorney, Agent, or Firm—Imre (Jim) Balogh; James A. Nicholson

[57] ABSTRACT

Disclosed are intranasal formulations comprising calcitonin and $\Delta$-aminolevulinic acid in a pharmaceutically acceptable excipient.

39 Claims, No Drawings

INTRANASAL CALCITONIN FORMULATIONS

BACKGROUND OF THE INVENTION

1. Field of the Invention

The present invention relates to a novel method of administering calcitonin to patients and to formulations adapted for nasal administration. More particularly, the present invention relates to calcitonin-containing pharmaceutical formulations having therein Δ-aminolevulinic acid which inhibits the degradation of calcitonin and enhances its bioavailability.

2. Description of the Prior Art

The method of administration of pharmaceutically active calcitonin is predominantly by injection, although efforts were made in the prior art to use other modes of administration. While administration by injection is acceptable for short-term therapy, administration by injection to patients in need of long-term calcitonin therapy has serious problems. Not only is it costly to patients to have physicians do the administration for extended periods of time, but it is also painful and inconvenient. Nor can calcitonin be given orally to patients since oral administration will result in degradation of calcitonin.

Recently, the prior art has found that calcitonin may also be administered via intranasal route and proposed various compositions for such administration. In general, calcitonin is in admixture with a pharmaceutically acceptable vehicle which may comprise an aqueous base, an oil-in-water or water-in-oil emulsion or an oily solvent base suitable for use on the mucous membranes, such as mineral or vegetable oils and fatty acid esters and one or more chemicals which are soluble in the base. While small molecular weight polypeptides, such as tripeptides and tetrapeptides, are efficiently absorbed intranasally, larger molecules, such as calcitonin, have been found to require the presence of absorption promoters to enhance absorption across mucous membranes. To that end, absorption promoters, such as chelating agents, surface active agents and the like are used in intranasal formulations. Notwithstanding their beneficial effects, some absorption promoters found to exhibit the undesirable property of producing irritation on the nasal membrane.

More recently, it has also been found that systemic bioavailability of calcitonin is limited not only by absorption factors but the extent of degradation of calcitonin into pharmacologically inactive fragments by the action of nasal mucosal peptidases.

As a result of extensive investigations of various formulations of calcitonin for intranasal administration, the present inventors have found that nasal mucosal peptidases may be inhibited by the use of Δ-aminolevulinic acid, when co-administered intranasally with calcitonin. Such co-administration may be accomplished using various pharmaceutically acceptable formulations suitable for nasal application.

SUMMARY OF THE INVENTION

This invention relates to an intranasal formulation comprising: from about 0.0001% w/v to about 15% w/v of calcitonin as hereinafter defined; from about 0.0005% w/v to about 10% w/v of Δ-aminolevulinic acid; and a pharmaceutically acceptable vehicle. The invention also relates to a method for increasing the bioavailability of calcitonin by inhibiting nasal mucosal peptidases utilizing Δaminolevulinic acid in the intranasal formulations.

According to the invention, there is also provided a method for the treatment of human patients suffering from diseases of hyperparathyroidism, idiopathic hypercalcemia of infancy, Paget's disease, vitamin D intoxication, or osteolytic bone metastases. Said diseases are characterized by hypercalcemia and high phosphate concentrations and their treatment is effected by decreasing serum calcium and phosphate concentrations in the blood by intranasal application of a calcitonin containing composition to effect control of said diseases by transephitelial action.

The term calcitonin as used herein means not only polypeptides having a structure corresponding to one of the naturally occurring hormones, and which may be naturally or synthetically produced, but also analogs thereof and related synthetic peptides having calcitonin activity.

DETAILED DESCRIPTION OF THE INVENTION

In accordance with the present invention, intranasal pharmaceutical formulations are provided in which the peptidase-inhibiting agent, Δ-aminolevulinic acid, is incorporated for enhancing the bioavailability of calcitonin. The composition of the formulations are described hereunder.

Calcitonin

Calcitonin is a polypeptide hormone involved in the control of calcium metabolism in the body. All known natural calcitonin peptides contain an amino acid sequence of 32 amino acids, of which the seven at the amino terminal end of the peptide chain are held in a cyclic configuration by a sulphur or carbon bridge and the carboxyl terminal residue consists of proline amide. The natural calcitonins include the salmon, eel, bovine, porcine, ovine, rat and human calcitonins. The detailed structure within the peptide chain of the hormone varies among different species and while the hormones, and their derivatives and analogues found in various species are of interest for use in the present invention, salmon calcitonin is of special interest in view of its relatively hydrophobic character and its stability. Salmon calcitonin has the following formula:

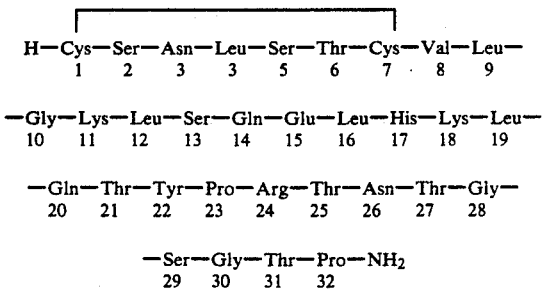

In U.S. Pat. Nos. 3,926,938, 4,062,815, 3,929,758, 4,033,940, 4,336,187, 4,388,235, 4,391,747 and 4,401,593 are disclosed improved synthesis of calcitonins including the salmon calcitonin referred to above.

Human, salmon and porcine calcitonins have been available for therapeutic use for several years. For example, synthetic salmon calcitonin is marketed by Armour Pharmaceutical Co. under the tradename CAL- CIMAR in a sterile, lyophilized form reconstitutable for subcutaneous or intravascular injection for the treatment of bone diseases.

The level of hypocalcemic activity of calcitonins varies from species to species. Salmon and chicken calcitonin have a potency of about 4,000 to 6,000 MCR (Medical Research Council) U/mg peptide; eel calcitonin about 2,000 to 4,000 MRC U/mg peptide; rat 400 MRC U/mg; while beef, sheep, hog and man about 100 to 200 MRC U/mg peptide.

Calcitonin used by the present invention may be obtained from Armour Pharmaceutical Co., from natural sources, or by synthetic routes known in the art. The synthesis can be performed by classical peptide synthesis as well as by solid phase synthesis.

In addition to the above-described calcitonins, the present invention encompasses synthetic calcitonin peptides having biological activity of the same type as those above-described. Such synthetic calcitonins are disclosed, along with processes for preparation thereof in the following U.S. Pat. Nos.

| | |
|---|---|
| 4,388,235 | 4,604,238 |
| 4,391,747 | 4,605,514 |
| 4,397,780 | 4,605,515 |
| 4,401,593 | 4,606,856 |
| 4,414,149 | 4,622,386 |
| 4,444,681 | 4,622,387 |
| 4,451,395 | 4,622,388 |
| 4,469,636 | 4,632,978 |
| 4,497,731 | 4,639,509 |
| 4,497,732 | 4,639,510 |
| 4,528,132 | 4,639,511 |
| 4,537,716 | 4,650,854 |
| 4,597,900 | 4,659,804 |
| 4,604,236 | 4,732,969 |
| 4,604,237 | 4,746,728 |

Synthetic calcitonin analogues disclosed in these patents are incorporated herein by reference as if set out in full herein. This list is not intended to be exhaustive of all U.S. Patents covering synthetic calcitonin analogues, but is representative of the analogues useful in the present invention; nor is the invention limited to the compounds disclosed in the listed patents.

In accordance for the foregoing, the following analogues of calcitonin constitute specific active ingredients used in the various intranasal formulations of the present invention:

1. Des asparagine-3-Calcitonins having the structures:

(a)
H—Cys—Ser—Leu—Ser—Thr—Cys—Val—Leu—Gly—Lys—
Leu—Ser—Gln—Glu—Leu—His—Lys—Leu—Gln—Thr—
Tyr—Pro—Arg—Thr—Asn—Thr—Gly—Ser—Gly—Thr—
Pro—NH$_2$;

(b)
Cys—Ser—Leu—Ser—Thr—Cys—Val—Leu—Gly—Lys—
Leu—Ser—Gln—Glu—Leu—His—Lys—Leu—Gln—Thr—
Tyr—Pro—Arg—Thr—Asp—Val—Gly—Ala—Gly—Thr—
Pro—NH$_2$.

2. [16-Alanine] Calcitonins having the following structures:

(a)
Cys—Ser—Asn—Leu—Ser—Thr—Cys—Val—Leu—Gly—
—Lys—Leu—Ser—Gln—Glu—Ala—His—Lys—Leu—Gln—
—Thr—Tyr—Pro—Arg—Thr—Asn—Thr—Gly—Ser—Gly—
—Thr—Pro—NH$_2$ (Salmon);

(b)
Cys—Ser—Asn—Leu—Ser—Thr—Cys—Val—Leu—Gly—
—Lys—Leu—Ser—Gln—Glu—Ala—His—Lys—Leu—Gln—
—Thr—Tyr—Pro—Arg—Thr—Asp—Val—Gly—Ala—Gly—
—Thr—Pro—NH$_2$ (Eel); and (c)
Cys—Gly—Asn—Leu—Ser—Thr—Cys—Met—Leu—Gly—
—Thr—Tyr—Thr—Gln—Asp—Ala—Asn—Lys—Phe—His—
—Thr—Phe—Pro—Gln—Thr—Ala—Ile—Gly—Val—Gly—
—Ala—Pro—NH$_2$ (Human).

3. Des $^2$-Glycine $^8$-Des $^{22}$-Calcitonins having the structures:

(a)
H—Cys—Asn—Leu—Ser—Thr—Cys—Gly—Leu—
—Gly—Lys—Leu—Ser—Gln—Glu—Leu—His—
—Lys—Leu—Gln—Thr—Pro—Arg—Thr—Asn—
—Thr—Gly—Ser—Gly—Thr—Pro—NH$_2$ (Salmon); and (b)
H—Cys—Asn—Leu—Ser—Thr—Cys—Gly—Leu—
—Gly—Lys—Leu—Ser—Gln—Glu—Leu—His—
—Lys—Leu—Gln—Thr—Pro—Arg—Thr—Asp—
—Val—Gly—Ala—Gly—Thr—Pro—Nh$_2$ (Eel).

4. Des-13-Serine-Calcitonins having the following structures:

(a)
Cys—Ser—Asn—Leu—Ser—Thr—Cys—Val—Leu—Gly—
—Lys—Leu—Gln—Glu—Leu—His—Lys—
—Leu—Gln—Thr—Tyr—Pro—Arg—Thr—Asn—
—Thr—Gly—Ser—Gly—Thr—Pro—NH$_2$;

(b)
Cys—Ser—Asn—Leu—Ser—Thr—Cys—Val—Leu—Gly—
—Lys—Leu—Gln—Glu—Leu—His—Lys—Leu—Gln—
—Thr—Tyr—Pro—Arg—Thr—Asp—Val—Gly—Ala—
—Gly—Thr—Pro—NH$_2$; and (c)
Cys—Gly—Asn—Leu—Ser—Thr—Cys—Met—Leu—Gly—
—Thr—Tyr—Gln—Asp—Phe—Asn—Lys—Phe—His—
—The—Phe—Pro—Gln—Thr—Ala—Ile—Gly—Val—
—Gly—Ala—Pro—NH$_2$.

5. Des-21-Threonine-Calcitonins having the following structures:

(a)
Cys—Ser—Asn—Leu—Ser—Thr—Cys—Val—Leu—Gly—
—Lys—Leu—Ser—Gln—Glu—Leu—His—Lys—Leu—Gln—
—Tyr—Pro—Arg—Thr—Asn—Thr—Gly—Ser—Gly—Thr—
—Pro—NH$_2$ (Salmon);

(b)
Cys—Ser—Asn—Leu—Ser—Thr—Cys—Val—Leu—Gly—
—Lys—Leu—Ser—Gln—Glu—Leu—His—Lys—Leu—Gln—
—Tyr—Pro—Arg—Thr—Asp—Val—Gly—Ala—Gly—Thr—
—Pro—NH$_2$, (Eel); and (c)
Cys—Gly—Asn—Leu—Ser—Thr—Cys—Met—Leu—Gly—
—Thr—Tyr—Thr—Gln—Asp—Phe—Asn—Lys—Phe—His—
—Phe—Pro—Gln—Thr—Ala—Ile—Gly—Val—Gly—Ala—

—Pro—NH₂ (Human).

6. [Gly², Ser³, Gly⁸, des-Tyr²²] Calcitonins having the following structures:

(a)
Cys—Gly—Ser—Leu—Ser—Thr—Cys—Gly—Leu—Gly—
—Lys—Leu—Ser—Gln—Glu—Leu—His—
—Lys—Leu—Gln—Thr—Pro—Arg—Thr—Asn—
—Thr—Gly—Ser—Gly—Thr—Pro—NH₂; and (b)
Cys—Gly—Ser—Leu—Ser—Thr—Cys—Gly—Lue—Gly—
—Lys—Leu—Ser—Gln—Glu—Leu—His—
—Lys—Leu—Gln—Thr—Pro—Arg—Thr—Asp—
—Val—Gly—Ala—Gly—Thr—Pro—NH₂.

7. Des-4-Leucine-Calcitonins having the following structures:

(a)
Cys—Ser—Asn—Ser—Thr—Cys—Val—Leu—Gly—Lys—
—Leu—Ser—Gln—Glu—Leu—His—Lys—Leu—Gln—Thr—
—Tyr—Pro—Arg—Thr—Asn—Thr—Gly—Ser—Gly—Thr—
—Pro—NH₂ (Salmon);

(b)
Cys—Ser—Asn—Ser—Thr—Cys—Val—Leu—Gly—Lys—
—Leu—Ser—Gln—Glu—Leu—His—Lys—Leu—Gln—Thr—
—Tyr—Pro—Arg—Thr—Asp—Val—Gly—Ala—Gly—Thr—
—Pro—NH₂ (Eel); and (c)
Cys—Gly—Asn—Ser—Thr—Cys—Met—Leu—Gly—Thr—
—Tyr—Thr—Gln—Asp—Phe—Asn—Lys—Phe—His—Thr—
—Phe—Pro—Gln—Thr—Ala—Ile—Gly—Val—Gly—Ala—
—Pro—NH₂ (Human).

8. Calcitonin-(1-23)-Peptide Amides having the following structures:

(a)
Cys—Ser—Asn—Leu—Ser—Thr—Cys—Val—Leu—Gly—
—Lys—Leu—Ser—Gln—Glu—Leu—His—Lys—Leu—
—Gln—Thr—Tyr—Pro—NH₂; and (b)
$R_1$ $R_2$
| |
Cys—Ser—Asn—Leu—Ser—Thr—Cys—Val—Leu—Gly—
Lys—Leu—Ser—Gln—Glu—Leu—His—Lys—Leu—Gln—
—Thr—Tyr—Pro—NH₂.

9. [Des-1-Amino,8-Glycine) Calcitonins having the following structures:

(a)
Bmp—Ser—Asn—Leu—Ser—Thr—Cys—Gly—Leu—Gly—
Lys—Leu—Ser—Gln—Glu—Leu—His—Lys—Leu—Gln—
Thr—Tyr—Pro—Arg—Thr—Asn—Thr—Gly—Ser—Gly—
—Thr—Pro—NH₂ (Salmon); and (b)
Bmp—Scr—Asn—Leu—Scr—Thr—Cys—Val—Leu—Gly—
Lys—Leu—Scr—Gln—Glu—Leu—His—Lys—Leu—Gln—
Thr—Tyr—Pro—Arg—Thr—Asp—Val—Gly—Ala—Gly—
—Thr—Pro—NH₂ (Eel).

10. [1,7-Di-Alanine] Calcitonins having the following structures:

(a)
Ala—Ser—Asn—Leu—Ser—Thr—Ala—Val—Leu—Gly—
Lys—Leu—Ser—Gln—Glu—Ala—His—Lys—Leu—Gln—
Thr—Tyr—Pro—Arg—Thr—Asn—Thr—Gly—Ser—Gly—
Thr—Pro—NH₂;

(b)
Ala—Ser—Asn—Leu—Ser—Thr—Ala—Val—Leu—Gly—
Lys—Leu—Ser—Gln—Glu—Ala—His—Lys—Leu—Gln—
Thr—Tyr—Pro—Arg—Thr—Asp—Val—Gly—Ala—Gly—
Thr—Pro—NH₂.

11. 8-Methionine Calcitonins having the following structures:

(a)
Cys—Ser—Asn—Leu—Ser—Thr—Cys—Met—Leu—
Gly—Lys—Leu—Ser—Gln—Glu—Leu—His—Lys—
Leu—Gln—Thr—Tyr—Pro—Arg—Thr—Asn—Thr—
Gly—Ser—Gly—Thr—Pro—NH₂; and (b)
Cys—Ser—Asn—Leu—Ser—Thr—Cys—Met—Leu—
Gly—Lys—Leu—Ser—Gln—Glu—Leu—His—Lys—
Leu—Gln—Thr—Tyr—Pro—Arg—Thr—Asp—Val—
Gly—Ala—Gly—Thr—Pro—NH₂.

12. Des-2Serine, 3-Asparagine Calcitonins having the following structures:

(a)
Cys—Leu—Ser—Thr—Cys—Val—Leu—Gly—Lys—
Leu—Ser—Gln—Glu—Leu—His—Lys—Leu—Gln—
Thr—Tyr—Pro—Arg—Thr—Asn—Thr—Gly—Ser—
Gly—Thr—Pro—NH₂; and (b)
Cys—Leu—Ser—Thr—Cys—Val—Leu—Gly—Lys—
Leu—Scr—Gln—Glu—Leu—His—Lys—Leu—Gln—
Thr—Tyr—Pro—Arg—Thr—Asp—Val—Gly—Ala—
Gly—Thr—Pro—NH₂.

13. G-Serine, Des-19-Leucine Calcitonins having the following structures:

(a)
Cys—Ser—Asn—Leu—Ser—Ser—Cys—Val—Leu—Gly—
Lys—Leu—Ser—Gln—Glu—Leu—His—Lys—Gln—Thr—
Tyr—Pro—Arg—Thr—Asn—Thr—Gly—Ser—
—Gly—Thr—Pro—NH₂; and (b)
Cys—Ser—Asn—Leu—Ser—Ser—Cys—Val—Leu—
Gly—Lys—Leu—Scr—Gln—Glu—Leu—His—Lys—Gln—
Thr—Tyr—Pro—Arg—Thr—Asp—Val—Gly—Ala—Gly—
—Thr—Pro—NH₂.

14. [16,19-Di-Alanine] Calcitonins having the following structures:

(a)
Cys—Ser—Asn—Leu—Ser—Thr—Cys—Val—Leu—Gly—
Lys—Leu—Ser—Gln—Glu—Ala—His—Lys—Ala—Gln—
Thr—Tyr—Pro—Arg—Thr—Asn—Thr—Gly—Ser—Gly—
—Thr—Pro—NH₂;

(b)
Cys—Ser—Asn—Leu—Ser—Thr—Cys—Val—Leu—Gly—
Lys—Leu—Ser—Gln—Glu—Ala—His—Lys—Ala—Gln—
Thr—Tyr—Pro—Arg—Thr—Asp—Val—Gly—Ala—Gly—
—Thr—Pro—NH₂.

15. (1-S-Acetamidomethyl Systeine, 7Alanine) Calcitonins having the following structures:

(a)
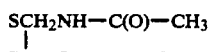
Cys—Ser—Asn—Leu—Ser—Thr—Ala—Val—Leu—Gly—
Lys—Leu—Ser—Gln—Glu—Leu—His—Lys—Leu—Gln—
Thr—Tyr—Pro—Arg—Thr—Asn—Thr—Gly—Ser—Gly—
—Thr—Pro—NH₂; and (b)
SCH₂NH—C(O)—CH₃
|
Cys—Ser—Asn—Leu—Ser—Thr—Ala—Val—Leu—Gly—
Lys—Leu—Ser—Gln—Glu—Leu—His—Lys—Leu—Gln—
Thr—Tyr—Pro—Arg—Thr—Asp—Val—Gly—Ala—Gly—
—Thr—Pro—NH₂.

16. Des-19-Leucine - Calcitonin Analogs having the following structures:

(a)
⌈⎯⎯⎯⎯⎯⎯⎯⎯⎯⎯⎯⌉
Cys—Ser—Asn—Leu—Ser—Thr—Cys—Val—Leu—
Gly—Lys—Leu—Ser—Gln—Glu—Leu—His—Lys—
Gln—Thr—Tyr—Pro—Arg—Thr—Asn—Thr—Gly—
—Ser—Gly—Thr—Pro—NH₂;

(b)
⌈⎯⎯⎯⎯⎯⎯⎯⎯⎯⎯⎯⌉
Cys—Ser—Asn—Leu—Ser—Thr—Cys—Val—Leu—
Gly—Lys—Leu—Ser—Gln—Glu—Leu—His—Lys—
Gln—Thr—Tyr—Pro—Arg—Thr—Asp—Val—Gly—
—Ala—Gly—Thr—Pro—NH₂.

17. (Bis-1,7-S-Acetamidomethyl-L-Systeine) Salmon Calcitonins having the following structures:

(a)
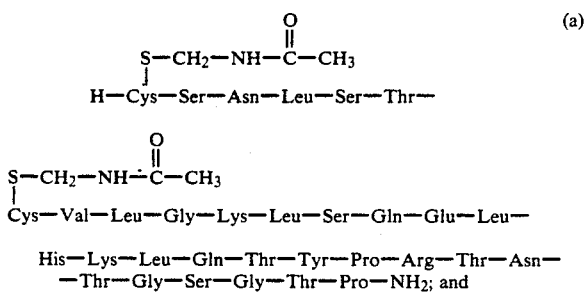
Cys—Val—Leu—Gly—Lys—Leu—Ser—Gln—Glu—Leu—
His—Lys—Leu—Gln—Thr—Tyr—Pro—Arg—Thr—Asn—
—Thr—Gly—Ser—Gly—Thr—Pro—NH₂; and (b)
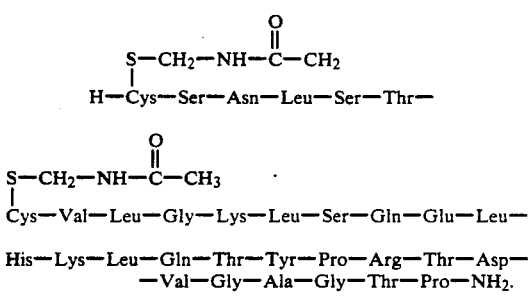
Cys—Val—Leu—Gly—Lys—Leu—Ser—Gln—Glu—Leu—
His—Lys—Leu—Gln—Thr—Tyr—Pro—Arg—Thr—Asp—
—Val—Gly—Ala—Gly—Thr—Pro—NH₂.

18. 8-Glycine, Des-19-Leucine-Calcitonins having the following structures:

(a)
⌈⎯⎯⎯⎯⎯⎯⎯⎯⎯⎯⎯⌉
Cys—Ser—Asn—Leu—Ser—Thr—Cys—Gly—Leu—Gly—
Lys—Leu—Ser—Gln—Glu—Leu—His—Lys—Gln—
Thr—Tyr—Pro—Arg—Thr—Asn—Thr—Gly—Ser—
—Gly—Thr—Pro—NH₂ (Salmon);

(b)
⌈⎯⎯⎯⎯⎯⎯⎯⎯⎯⎯⎯⌉
Cys—Ser—Asn—Leu—Ser—Thr—Cys—Gly—Leu—Gly—
Lys—Leu—Ser—Gln—Glu—Leu—His—Lys—Gln—
Thr—Tyr—Pro—Arg—Thr—Asp—Val—Gly—Ala—
—Gly—Thr—Pro—NH₂ (Eel); and (c)
⌈⎯⎯⎯⎯⎯⎯⎯⎯⎯⎯⎯⌉
Cys—Ala—Ser—Leu—Ser—Thr—Cys—Gly—Leu—Gly—
Lys—Leu—Ser—Gln—Glu—Leu—His—Lys—Gln—
Thr—Tyr—Pro—Arg—Thr—Asp—Val—Gly—Ala—
—Gly—Thr—Pro—NH₂ (Chicken).

19. Des-Leu$^{16}$-Calcitonins having the following structures:

(a)
⌈⎯⎯⎯⎯⎯⎯⎯⎯⎯⎯⎯⌉
Cys—Ser—Asn—Leu—Ser—Thr—Cys—Val—Leu—Gly—
Lys—Leu—Ser—Gln—Glu—His—
Lys—Leu—Gln—Thr—Tyr—Pro—Arg—
Thr—Asn—Thr—Gly—Ser—Gly—Thr
—Pro—NH₂ (Salmon);

(b)
⌈⎯⎯⎯⎯⎯⎯⎯⎯⎯⎯⎯⌉
Cys—Ser—Asn—Leu—Ser—Thr—Cys—Val—Leu—Gly—
Lys—Leu—Ser—Gln—Glu—His—
Lys—Leu—Gln—Thr—Tyr—Pro—Arg—
Thr—Asp—Val—Gly—Ala—Gly—Thr—
—Pro—NH₂ (Eel);

(c)
⌈⎯⎯⎯⎯⎯⎯⎯⎯⎯⎯⎯⌉
Cys—Gly—Asn—Leu—Ser—Thr—Cys—Met—Leu—Gly—
Thr—Tyr—Thr—Gln—Asp—Asn—
Lys—Phe—His—Thr—Phe—Pro—Glu—
Thr—Ala—Ile—Gly—Val—Gly—Ala—
—Pro—NH₂ (Human).

20. Leucine$^{22}$ — Calcitonins having the following structures:

(a)
⌈⎯⎯⎯⎯⎯⎯⎯⎯⎯⎯⎯⌉
H—Cys—Ser—Asn—Leu—Ser—Thr—Cys—Val—Leu—Gly—
Lys—Leu—Ser—Gln—Glu—Leu—His—Lys—Leu—Gln—
—Thr—Leu—Pro—Arg—Thr—Asn—Thr—Gly—Ser—Gly—
—Thr—Pro—NH₂ (Salmon); and (b)
⌈⎯⎯⎯⎯⎯⎯⎯⎯⎯⎯⎯⌉
H—Cys—Ser—Asn—Leu—Ser—Thr—Cys—Val—Leu—Gly—
—Lys—Leu—Ser—Gln—Glu—Leu—His—Lys—Leu—Gln—
—Thr—Leu—Pro—Arg—Thr—Asp—Val—Gly—Ala—Gly—
—Thr—Pro—NH₂ (Eel).

21. Glycine — 8 Calcitonins having the following structures:

(a)
⌈⎯⎯⎯⎯⎯⎯⎯⎯⎯⎯⎯⌉
H—Cys—Ser—Asn—Leu—Ser—Thr—Cys—Gly—Leu—
—Gly—Lys—Leu—Ser—Gln—Glu—Leu—His—Lys—Leu—
—Gln—Thr—Tyr—Pro—Arg—Thr—Asn—Thr—Gly—Ser—
—Gly—Thr—Pro—NH₂; and

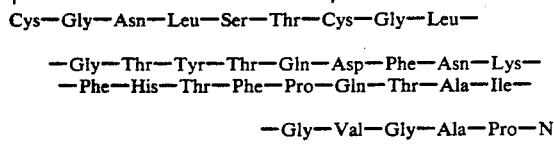

22. Glycine[8]-D-Arginine[24] Calcitonins having the following structures:

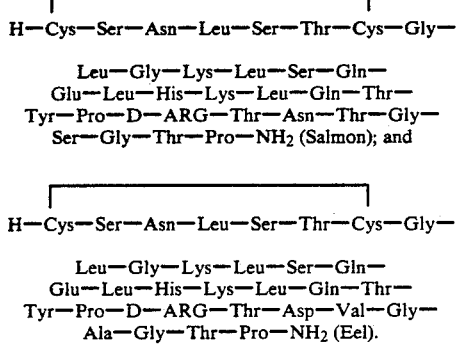

23. L-Tyrosine[21] Calcitonins having the following structures:

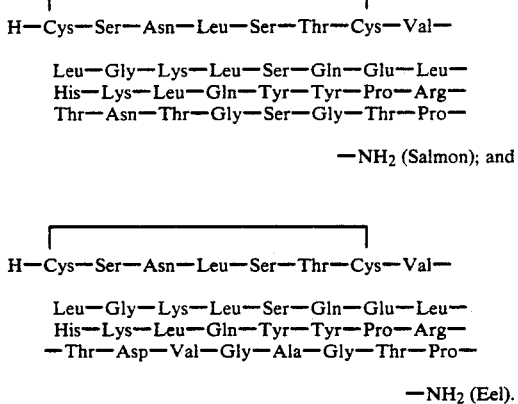

24. D-Arginine[24] Calcitonins having the following structures:

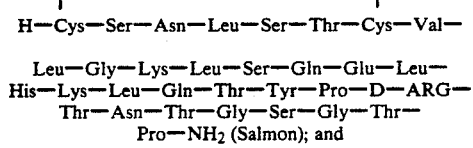

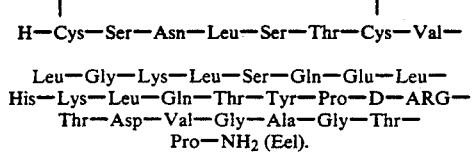

25. Amides Analogues of Calcitonin having the following structures:

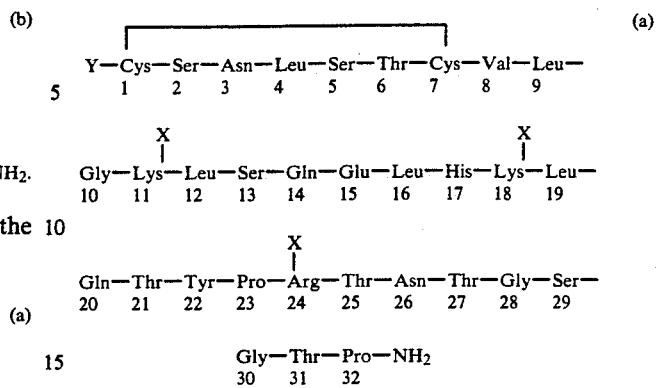

wherein Y is N(a) decanoyl and X is N(e) decanoyl.

26. [N-alpha, 1, 7-Di-Alanine, Des-19-Leucine] Calcitonins having the following structures:

[N-alpha-X, 1, 7 Di-Alanine (8-Y)  (a)
Des-19-Leucine] calcitonins, wherein

X is H, free amino or acyl-amino wherein acyl is derived from a carboxylic acid having 1-10 carbon atoms, L-lactic acid or half amide of malonic, succinic, glutaric, or adipic acids, and Y is L-valine, glyine, L-methonine, L-alanine, L-leucine or L isoleucine; and

[N-alpha-X, 1, 7-Di-Alanine, Des-19-Leucine]  (b)
calcitonins, wherein

X is an acyl derived rom carboxylic acid having $C_{1-5}$ carbon atoms.

27. 1,7-Di-Alanine, 8-Glycine, Des-19-Leucine Calcitonin having the following structure:

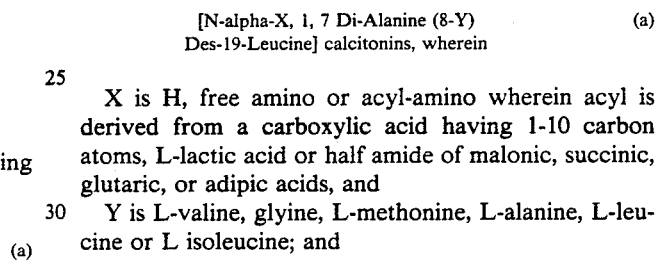

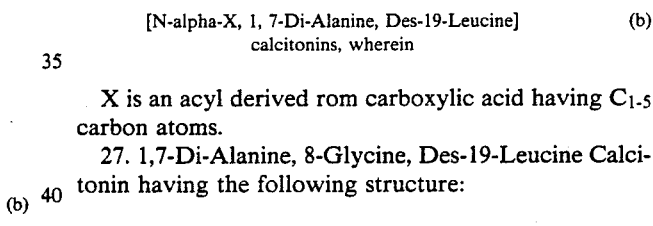

28. Nα-Propionyl, 1,7-Di-Alanine, Des-19- Leucine Calcitonin having the following structure:

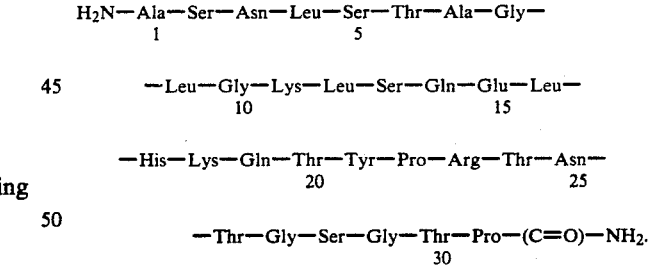

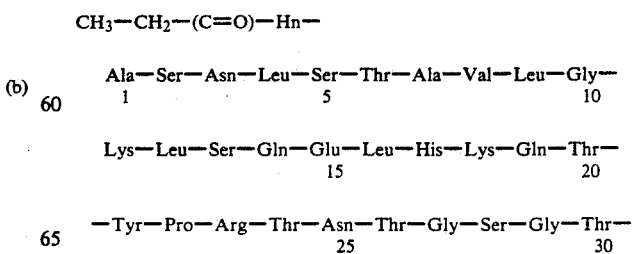

Δ-Aminolevulinic Acid

Enhancement of intranasal delivery of calcitonin is effected by the presence of Δ-aminolevulinic acid in the formulations of the present invention.

Δ-aminolevulinic acid, having the formula: $H_2N\text{-}CH_2\text{-}C(O)\text{-}CH_2\text{-}CH_2\text{-}CO_2H$, occurs naturally in the body, being derived from the condensation of glycine with succinyl-SCoA. It is known as a precursor of vitamins $B_{12}$, heme and chlorophyll. Its method of preparation is known in the art, for example, U.S.P. No. 3,846,490.

Vehicles

The biologically/pharmacologically active calcitonins, as hereinbefore defined, and Δ-aminolevulinic acid will be formulated with one or more pharmaceutically acceptable excipients which result in a composition suitable for administering the calcitonin across the nasal membranes as a spray, nose drop or aerosol.

The diluent base or vehicle used in accordance with the present invention may be non-aqueous or aqueous. In the former case the group of diluents is the physiologically acceptable polar solvents. Preferred compounds of this type are those with which it is possible to make a solution of adequate concentration of dissolved calcitonin. Examples of these agents are vegetable and mineral oils. If desired, such non-aqueous media may be mixed with water to form the diluent of the preparation. However, the degree of physiological acceptability of the non-aqueous diluents is generally less than that of aqueous media and the preferred diluent is therefore water without the addition of organic solvents.

Preferably, the subject calcitonin is formulated in water or a pharmaceutically acceptable aerosol composition. Nasal spray solutions are especially preferred with water or in buffer at a ph of between about 3.0 to 8.0, using a pharmaceutically acceptable buffer system. The buffer system of the present invention preferably contain a sodium or potassium phosphate/phosphoric acid buffer or a sodium or potassium acetate/acetic acid buffer or a sodium or potassium citrate/citric acid buffer in the range of 0.01 M to 0.5 M and preferably in the range of 0.05M to 0.2M. This concentration was found effective to provide stability of the dissolved calcitonin in the diluent base or vehicle.

The preparations of the present invention may also contain other additives, such as antioxidants, stabilizers, tonicity adjusters, viscosity builders, preservatives, and the like. The concentration of these additives may vary according to the particular additive used and the desired result sought. In general the concentrations for these additives will be in the range as follows:

| Additives | % W/V |
|---|---|
| Antioxidants | 0.01–0.2 |
| Stabilizers | 0.01–2.0 |
| Tonicity Adjuster | 0.01–0.5 |
| Viscosity Builders | 0.1–2.0 |
| Preservatives | 0.001–2.0 |

While the use of the kind and concentration of additives will be well within the ability of the skilled artisan, the following will serve as illustration for two additives generally used in pharmaceutical preparations intended for similar purposes.

| | % W/V |
|---|---|
| Preservatives | |
| Benzalkonium chloride | 0.004–0.02 |
| Disodium ethylene diamine tetraacetate | 0.01–0.2 |
| Thimerosal | 0.001–0.01 |
| Chlorobutanol | 0.5–1.0 |
| Methyl and/or propyl paraben | 0.01–0.2 |
| Phenethyl alcohol | 0.25–0.75 |
| Cyclohexedine | 0.01–0.1 |
| Viscosity Agents | |
| Methyl cellulose | 0.1–2.0 |
| Hydroxyethyl cellulose | 0.1–2.0 |
| Hydroxypropyl cellulose | 0.1–2.0 |
| Polyvinylpyrrolidone | 0.5–2.0 |

Aerosol formulations and nose drops are prepared as per known techniques and composition profiles practiced in the art.

In preparing the formulations of the present invention, calcitonin may be dissolved in the vehicle or diluent after which the additional ingredients are added in accordance with customary formulation procedures known in the pharmaceutical industry.

Examples of typical intranasal formulations are set forth below. However, it is to be understood that these examples are given by way of illustration only and are not to be construed as limiting the invention either in spirit or in scope as many modifications will be apparent to those skilled in the art.

| | % W/V |
|---|---|
| EXAMPLE 1 | |
| Calcitonin[1] | 0.009 |
| Δ-aminolevulinic acid | 0.5 |
| Gelatin | 1.0 |
| Purified water q.s. | 100 |
| EXAMPLE 2 | |
| Calcitonin[1] | 0.009 |
| Δ-aminolevulinic acid | 1.0 |
| Gelatin | 1.0 |
| Purified water q.s. | 100 |
| EXAMPLE 3 | |
| Calcitonin[1] | 0.25 |
| Δ-aminolevulinic acid | 1.5 |
| Sodium acetate.$3H_2O$ | 1.36 |
| Acetic acid | 0.6 |
| Purified water q.s. | 100 |
| EXAMPLE 4 | |
| Calcitonin[1] | 0.5 |
| Δ-aminolevulinic acid | 2.0 |
| Sodium acetate.$3H_2O$ | 1.36 |
| Acetic acid | 0.6 |
| Purified water q.s. | 100 |
| EXAMPLE 5 | |
| Calcitonin[1] | 0.003 |
| Δ-aminolevulinic acid | 3.0 |
| Sodium acetate.$3H_2O$ | 1.36 |
| Acetic acid | 0.6 |
| Purified water q.s. | 100 |
| EXAMPLE 6 | |
| Calcitonin[2] | 0.25 |
| Δ-aminolevulinic acid | 1.0 |
| Sodium citrate | 1.36 |
| Citric acid | 0.6 |
| Purified water q.s. | 100 |
| EXAMPLE 7 | |
| Calcitonin[3] | 0.50 |
| Δ-aminolevulinic acid | 2.0 |
| Sodium phosphate | 2.40 |
| Citric acid | 0.34 |
| Thimerosal | 0.002 |
| Purified water q.s. | 100 |

-continued

EXAMPLE 8
| | |
|---|---|
| Calcitonin[4] | 2.0 |
| Δ-aminolevulinic acid | 0.5 |
| Sodium acetate.3H$_2$O | 1.36 |
| Acetic acid | 0.6 |
| Benzalkonium chloride | 0.01 |
| Disodium ethylenediamine tetraacetate | 0.1 |
| Purified water q.s. | 100 |

EXAMPLE 9
| | |
|---|---|
| Calcitonin[5] | 5.00 |
| Δ-aminolevulinic acid | 3.00 |
| Sodium acetate.3H$_2$O | 1.36 |
| Acetic acid | 1.36 |
| Chlorobutanol | 0.1 |
| Phenethyl alcohol | 0.2 |
| Purified water q.s. | 100 |

EXAMPLE 10
| | |
|---|---|
| Calcitonin[6] | 10.0 |
| Δ-aminolevulinic acid | 7.0 |
| Sodium phosphate | 2.40 |
| Citric acid | 0.34 |
| Thimerosal | 0.002 |
| Purified water q.s. | 100 |

Amount per 1 ml

EXAMPLE 11
| | |
|---|---|
| Calcitonin[7] | 1428.0 I.U. |
| Δ-aminolevulinic acid | 10.0 mg |
| Benzalkonium chloride solution, N.F., 50% | 0.20 mg |
| Sodium acetate | 2.95 mg |
| Acetic acid | 9.84 mg |
| Hydrochloric acid, ACS } If needed | To adjust pH to 4.0 |
| Sodium hydroxide, ACS | To adjust pH to 4.0 |
| Water for injection, USP | q.s. to 1 ml |

EXAMPLE 12
| | |
|---|---|
| Calcitonin[7] | 1428.0 I.U. |
| Δ-aminolevulinic acid | 5.0 mg |
| Benzalkonium chloride solution, N.F., 50% | 0.20 mg |
| Sodium acetate | 2.95 mg |
| Acetic acid | 9.84 mg |
| Hydrochloric acid, ACS } If needed | To adjust pH to 4.0 |
| Sodium hydroxide, ACS | To adjust pH to 4.0 |
| Water for injection, USP | q.s. to 1 ml |

EXAMPLE 13
| | |
|---|---|
| Calcitonin[8] | 1428.0 I.U. |
| Δ-aminolevulinic acid | 10.0 mg |
| Benzalkonium chloride solution, N.F., 50% | 0.20 mg |
| Disodium EDTA, USP | 1.00 mg |
| Citric acid monohydrate, USP | 12.19 mg |
| Sodium citrate dihydrate, USP | 12.37 mg |
| Hydrochloric acid, ACS } If needed | To adjust pH to 4.0 |
| Sodium hydroxide, ACS | To adjust pH to 4.0 |
| Water for injection, USP | q.s. to 1 ml |

EXAMPLE 14
| | |
|---|---|
| Calcitonin[8] | 1428.0 I.U. |
| Δ-aminolevulinic acid | 5.0 mg |
| Benzalkonium chloride solution, N.F., 50% | 0.20 mg |
| Disodium EDTA, USP | 1.00 mg |
| Citric acid monohydrate, USP | 12.19 mg |
| Sodium citrate dihydrate, USP | 12.37 mg |
| Hydrochloric acid, ACS } If needed | To adjust pH to 4.0 |
| Sodium hydroxide, ACS | To adjust pH to 4.0 |
| Water for injection, USP | q.s. to 1 ml |

The gelatin used in the above formulations is a standard hydrolipid animal gelatin prepared for pharmaceutical use and routinely used as a diluent for peptides.

[1] Synthetic salmon calcitonin having a potency of 4,000 MRC (Medical Research Council) units.

[2] Des asparagine-3-calcitonin; 4,300 MRC units/mg; USP 4,391,747.

[3] 1A-endo-glycine-calcitonin; 4,650 IU/mg; USP 4,497,732.

[4] 16-alanine calcitonin; 6,200 IU/mg; USP 4,528,132.

[5] glycine$^8$-D-arginine$^{24}$ calcitonin; 3,500 IU/mg; USP 4,414,149.

[6] D-arginine$^{24}$ calcitonin; 5,000 IU/mg; USP 4,469,632.

[7] 1,7-Di-alanine, 8-glycine, des-19-leucine calcitonin.

[8] Nα- Propionyl, 1,7-di-alanine, des-19-leucine calcitonin.

Testing for Bioavailability

According to the present invention, it has been found that calcitonin can be administered intranasally from a vehicle containing Δ-aminolevulinic acid as peptidase inhibitor with results considerably superior to those obtained with the administration of calcitonin without Δ-aminolevulinic acid. The following study illustrates the bioavailability of calcitonin from the formulations of the present invention.

Formulations

The test formulations contained salmon calcitonin (from Armour Pharmaceutical Co., Fort Washington, Pa.) in amounts of 1.5 U/100 μl, yielding a dose of 5 U/kg when the dose volume administered to animals was 50 μl/150 g body weight. The formulations were made in 0.2M acetate buffer at pH 4.1 and also contained Δ-aminolevulinic acid in concentrations of 1 mg/ml, 5 mg/ml and 10 mg/ml.

The control formulations were the same as the test formulations but lacked Δ-aminolevulinic acid.

Protocol

Male Sprague-Dawley rats (Charles River CD strain) weighing approximately 150 g at the time of dosing were obtained from Charles River Breeding Laboratories (Wilmington, Me). The rats were fasted over-night before use, and water was given ad libitum.

The rats were anesthetized with an intraperitoneal injection of pentobarbital (50 mg/kg). An external jugular vein was cannulated to facilitate periodic blood sampling. Before dosing, the nasopalatine apertures were closed with an adhesive agent (Krazy Glue, Krazy Glue Inc., Itasca, Ill.). Throughout the experiment, the animals were kept immobilized in a supine position by taping the animal on a dissection board.

The rats were then administered an intra-nasal dose of SCT (5U/kg, 50 μl/150 g) with or without the coadministration of Δ-aminolevulinic acid. The dosing was facilitated with the use of a micro-syringe (Hamilton Co., Reno, Nev.), and the dosing solution was delivered drop-wise into the nostril.

A volume of 0.7 ml of blood was drawn via the jugular cannula at 0 hours, and at 1.0, 2.0, 3.0, and 4.0 hours, post-dose. The samples were assayed for serum calcium according to an automated alizarin procedure as described by C.S. Fring et. al, Clin. Chem., 16, 816 (1970).

The results are shown in Table I.

TABLE I

The Effect of Coadministration of
Δ-Aminolevulinic Acid with an Intra-Nasal Dose
of SCT (5 U/kg) on the Enhancement of
Hypercalcemia in Rats

| Concentration of Δ-Aminole- vulinic Acid | $N^1$ | Max Hypocalcemia ± S.D. (%) | $Tmax^2$ (hr) |
|---|---|---|---|
| Control | 16 | 16.6 ± 8.2 | 2.0 |
| (1 mg/ml) | 14 | 25.2 ± 3.7 | 2.0 |
| (5 mg/ml) | 7 | 30.1 ± 3.3 | 3.0 |
| (10 mg/ml) | 8 | 26.7 ± 5.9 | 3.0 |

[1] Number of animals
[2] The time at which maximum hypocalcemia occurred.

While only certain embodiments of our invention have been described in specific detail, it will be apparent to those skilled in the art that many other specific embodiments may be practiced and many changes may be made all within the spirit of the invention and the scope of the appended claims.

What is claimed is:

1. An intranasal composition comprising from about 0.0001% W/V to about 15% W/V of a polypeptide having calcitonin activity (as hereinbefore defined); from about 0.0005% W/V to about 10% W/V of Δ-aminolevulinic acid; and a pharmaceutically acceptable excipient in a quantity to make volume.

2. The intranasal composition of claim 1 wherein said polypeptide is salmon calcitonin.

3. The intranasal composition of claim 1 wherein said polypeptide is an analog of salmon calcitonin.

4. The intranasal composition of claim 1 wherein said polypeptide is selected from the group consisting of eel, bovin, porcine, ovine, rat, chicken, and human calcitonins.

5. The composition of claim 1 wherein said polypeptide is obtained from natural sources.

6. The composition of claim 1 wherein said polypeptide is obtained by a synthetic route.

7. The intranasal composition of claim 1 wherein said polypeptide has a potency of from about 100 to about 10,000 international units per mg of polypeptide.

8. A method for enhancing the bioavailability of a polypeptide having calcitonin activity comprising: adding from about 0.0005% W/V to about 10% W/V of Δ-aminolevulinic acid to an intranasal composition comprising 0.0001% W/V to 15% W/V of a polypeptide having calcitonin activity and a pharmaceutically acceptable excipient in a quantity sufficient to make volume.

9. A method for the treatment of a patient suffering from diseases of hyperparathyroidism, idiopathic hypercalcemia of infancy, Paget's disease, vitamin D intoxication, or osteolytic bone maetastases, said diseases characterized by hypercalcemia and high phosphate concentrations in the blood of said patient comprising: intranasally administering to said patient in need of such treatment to effect control of at least one of said diseases an effective amount of the composition of claim 1.

10. An intranasal composition comprising: from about 0.0025% W/V to about 10% W/V of a polypeptide having calcitonin activity; from about 0.0025% W/V to about 10% W/V of Δ-aminolevulinic acid; and a pharmaceutically acceptable excipient in a quantity to make volume.

11. The intranasal composition of claim 10 wherein said polypeptide is

[N—alpha—X, 1, 7 Di—Alanine (8—Y) Des—19—Leucine] calcitonin, wherein

X is H, free amino or acyl-amino wherein acyl is derived from a carboxylic acid having 1–10 carbon atoms, L-lactic acid or half amide of malonic, succinic, glutaric, or adipic acids, and Y is L-valine, glycine, L-methonine, L-alanine, L-leucine or L isoleucine.

12. The intranasal composition of claim 10 wherein said polypeptide is:

[N—alpha—X, 1, 7—Di—Alanine, Des—19—Leucine] calcitonin, wherein

X is an acyl derived from carboxylic acid having $C_{1-5}$ carbon atoms.

13. The intranasal composition of claim 10 wherein said polypeptide is:

H—Cys—Ser—Leu—Ser—Thr—Cys—Val—Leu—Gly—
Lys—Leu—Ser—Gln—Glu—Leu—His—Lys—Leu—Gln—
Thr—Tyr—Pro—Arg—Thr—Asn—Thr—Gly—Ser—Gly—
Thr—Pro—NH₂.

14. The intranasal composition of claim 10 wherein said polypeptide is:

Cys—Ser—Asn—Leu—Ser—Thr—Cys—Val—Leu—Gly—
—Lys—Leu—Ser—Gln—Glu—Ala—His—Lys—Leu—Gln—
—Thr—Tyr—Pro—Arg—Thr—Asn—Thr—Gly—Ser—Gly—
—Thr—Pro—NH₂ (Salmon).

15. The intranasal composition of claim 10 wherein said polypeptide is:

H—Cys—Asn—Leu—Ser—Thr—Cys—Gly—Leu—
—Gly—Lys—Leu—Ser—Gln—Glu—Leu—His—
—Lys—Leu—Gln—Thr—Pro—Arg—Thr—Asn—
—Thr—Gly—Ser—Gly—Thr—Pro—NH₂ (Salmon).

16. The intranasal composition of claim 10 wherein said polypeptide is:

Cys—Ser—Asn—Leu—Ser—Thr—Cys—Val—Leu—Gly—
—Lys—Leu—Gln—Glu—Leu—His—Lys—
—Leu—Gln—Thr—Tyr—Pro—Arg—Thr—Asn—
—Thr—Gly—Ser—Gly—Thr—Pro—NH₂.

17. The intranasal composition of claim 10 wherein said polypeptide is:

Cys—Ser—Asn—Leu—Ser—Thr—Cys—Val—Leu—Gly—
—Lys—Leu—Ser—Gln—Glu—Leu—His—Lys—Leu—
—Gln—Tyr—Pro—Arg—Thr—Asn—Thr—Gly—Ser—
—Gly—Thr—Pro—NH₂ (Salmon).

18. The intranasal composition of claim 10 wherein said polypeptide is:

```
┌─────────────────────────────────────────────────┐
Cys—Gly—Ser—Leu—Ser—Thr—Cys—Gly—Leu—Gly—
  —Lys—Leu—Ser—Gln—Glu—Leu—His—
    —Lys—Leu—Gln—Thr—Pro—Arg—Thr—Asn—
      —Thr—Gly—Ser—Gly—Thr—Pro—NH₂.
```

19. The intranasal composition of claim 10 wherein said polypeptide is:

```
┌─────────────────────────────────────────────────┐
Cys—Ser—Asn—Ser—Thr—Cys—Val—Leu—Gly—Lys—
  —Leu—Ser—Gln—Glu—Leu—His—Lys—Leu—Gln—
    —Thr—Tyr—Pro—Arg—Thr—Asn—Thr—Gly—Ser—
      —Gly—Thr—Pro—NH₂ (Salmon).
```

20. The intranasal composition of claim 10 wherein said polypeptide is:

```
┌─────────────────────────────────────────────────┐
Cys—Ser—Asn—Leu—Ser—Thr—Cys—Val—Leu—Gly—
  —Lys—Leu—Ser—Gln—Glu—Leu—His—Lys—Leu—
    —Gln—Thr—Tyr—Pro—NH₂.
```

21. The intranasal composition of claim 10 wherein said polypeptide is:

```
┌─────────────────────────────────────────────────┐
Bmp—Ser—Asn—Leu—Ser—Thr—Cys—Gly—Leu—Gly—
Lys—Leu—Ser—Gln—Glu—Leu—His—Lys—Leu—Gln—
Thr—Tyr—Pro—Arg—Thr—Asn—Thr—Gly—Ser—Gly—
  —Thr—Pro—NH₂ (Salmon).
```

22. The intranasal composition of claim 10 wherein said polypeptide is:

Ala—Ser—Asn—Leu—Ser—Thr—Ala—Val—Leu—Gly—
Lys—Leu—Ser—Gln—Glu—Ala—His—Lys—Leu—Gln—
Thr—Tyr—Pro—Arg—Thr—Asn—Thr—Gly—Ser—Gly—
Thr—Pro—NH₂.

23. The intranasal composition of claim 10 wherein said polypeptide is:

```
┌─────────────────────────────────────────────────┐
Cys—Ser—Asn—Leu—Ser—Thr—Cys—Met—Leu—
Gly—Lys—Leu—Ser—Gln—Glu—Leu—His—Lys—
Leu—Gln—Thr—Tyr—Pro—Arg—Thr—Asn—Thr—
Gly—Ser—Gly—Thr—Pro—NH₂.
```

24. The intranasal composition of claim 10 wherein said polypeptide is:

```
┌─────────────────────────────────────────────────┐
Cys—Leu—Ser—Thr—Cys—Val—Leu—Gly—Lys—
Leu—Ser—Gln—Glu—Leu—His—Lys—Leu—Gln—
Thr—Tyr—Pro—Arg—Thr—Asn—Thr—Gly—Ser—
Gly—Thr—Pro—NH₂.
```

25. The intranasal composition of claim 10 wherein said polypeptide is:

```
  R₁                          R₂
  |                           |
Cys—Ser—Asn—Leu—Ser—Ser—Cys—Val—Leu—Gly—
Lys—Leu—Ser—Gln—Glu—Leu—His—Lys—Gln—Thr—
Tyr—Pro—Arg—Thr—Asn—Thr—Gly—Ser—Gly—Thr—
Pro—NH₂;
``` where $R_1$ is S-n-alkyl, Cys or H and $R_2$ is S-n-alkyl or H, $R_1$ being S-n-alkyl, Cys or H when $R_2$ is H and $R_2$ being S-n-alkyl or H when $R_1$ is H.

26. The intranasal composition of claim 10 wherein said polypeptide is:

```
┌─────────────────────────────────────────────────┐
Cys—Ser—Asn—Leu—Ser—Ser—Cys—Val—Leu—Gly—
Lys—Leu—Ser—Gln—Glu—Leu—His—Lys—Gln—Thr—
Tyr—Pro—Arg—Thr—Asn—Thr—Gly—Ser—
  —Gly—Thr—Pro—NH₂.
```

27. The intranasal composition of claim 10 wherein said polypeptide is:

```
SCH₂NH—C(O)—CH₃
|
Cys—Ser—Asn—Leu—Ser—Thr—Ala—Val—Leu—Gly—
Lys—Leu—Ser—Gln—Glu—Leu—His—Lys—Leu—Gln—
Thr—Tyr—Pro—Arg—Thr—Asn—Thr—Gly—Ser—Gly—
  —Thr—Pro—NH₂.
```

28. The intranasal composition of claim 10 wherein said polypeptide is:

```
┌─────────────────────────────────────────────────┐
Cys—Ser—Asn—Leu—Ser—Thr—Cys—Val—Leu—
Gly—Lys—Leu—Ser—Gln—Glu—Leu—His—Lys—
Gln—Thr—Tyr—Pro—Arg—Thr—Asn—Thr—Gly—
  —Ser—Gly—Thr—Pro—NH₂.
```

29. The intranasal composition of claim 10 wherein said polypeptide is:

```
            O
            ||
     S—CH₂—NH—C—CH₃
     |
H—Cys—Ser—Asn—Leu—Ser—Thr—
            O
            ||
     S—CH₂—NH—C—CH₃
     |
Cys—Val—Leu—Gly—Lys—Leu—Ser—Gln—Glu—Leu—
His—Lys—Leu—Gln—Thr—Tyr—Pro—Arg—Thr—Asn—
  —Thr—Gly—Ser—Gly—Thr—Pro—NH₂.
```

30. The intranasal composition of claim 10 wherein said polypeptide is:

```
┌─────────────────────────────────────────────────┐
Cys—Ser—Asn—Leu—Ser—Thr—Cys—Gly—Leu—Gly—
Lys—Leu—Ser—Gln—Glu—Leu—His—Lys—Gln—
Thr—Tyr—Pro—Arg—Thr—Asn—Thr—Gly—Ser—
  —Gly—Thr—Pro—NH₂ (Salmon).
```

31. The intranasal composition of claim 10 wherein said polypeptide is:

```
    ┌─────────────────────────┐
    Cys—Ser—Asn—Leu—Ser—Thr—Cys—Val—Leu—Gly—
    Lys—Leu—Ser—Gln—Glu—His—
    Lys—Leu—Gln—Thr—Tyr—Pro—Arg—
    Thr—Asn—Thr—Gly—Ser—Gly—Thr—
              —Pro—NH₂ (Salmon).
```

32. The intranasal composition of claim 10 wherein said polypeptide is:

```
      ┌──────────────────────────┐
    H—Cys—Ser—Asn—Leu—Ser—Thr—Cys—Val—Leu—Gly—
    Lys—Leu—Ser—Gln—Glu—Leu—His—Lys—Leu—Gln—Thr—
    Leu—Pro—Arg—Thr—Asn—Thr—Gly—Ser—Gly—Thr—Pro—
    NH₂ (Salmon).
```

33. The intranasal composition of claim 10 wherein said polypeptide is:

```
      ┌──────────────────────────┐
    H—Cys—Ser—Asn—Leu—Ser—Thr—Cys—Gly—Leu—Gly—
    Lys—Leu—Ser—Gln—Glu—Leu—His—Lys—Leu—Gln—
    Thr—Tyr—Pro—Arg—Thr—Asn—Thr—Gly—Ser—Gly—
    Thr—Pro—NH₂.
```

34. The intranasal composition of claim 10 wherein said polypeptide is:

```
      ┌──────────────────────────┐
    H—Cys—Ser—Asn—Leu—Ser—Thr—Cys—Gly—
    Leu—Gly—Lys—Leu—Ser—Gln—
    Glu—Leu—His—Lys—Leu—Gln—Thr—
    Tyr—Pro—D—ARG—Thr—Asn—Thr—Gly—
    Ser—Gly—Thr—Pro—NH₂ (Salmon).
```

35. The intranasal composition of claim 10 wherein said polypeptide is:

```
      ┌──────────────────────────┐
    H—Cys—Ser—Asn—Leu—Ser—Thr—Cys—Val—
    Leu—Gly—Lys—Leu—Ser—Gln—Glu—Leu—
    His—Lys—Leu—Gln—Tyr—Tyr—Pro—Arg—
    Thr—Asn—Thr—Gly—Ser—Gly—Thr—Pro—NH₂ (Salmon).
```

36. The intranasal composition of claim 10 wherein said polypeptide is:

```
        ┌──────────────────────────┐
    H—Cys—Ser—Asn—Leu—Ser—Thr—Cys—Val—
    Leu—Gly—Lys—Leu—Ser—Gln—Glu—Leu—
    His—Lys—Leu—Gln—Thr—Tyr—Pro—D—ARG—
    Thr—Asn—Thr—Gly—Ser—Gly—Thr—
         Pro—NH₂ (Salmon).
```

37. The intranasal composition of claim 10 wherein said polypeptide is:

```
    Y—Cys—Ser—Asn—Leu—Ser—Thr—Cys—Val—Leu—
       1   2   3   4   5   6   7   8   9
         X                             X
         |                             |
    Gly—Lys—Leu—Ser—Gln—Glu—Leu—His—Lys—Leu—
    10  11  12  13  14  15  16  17  18  19
                          X
                          |
    Gln—Thr—Tyr—Pro—Arg—Thr—Asn—Thr—Gly—Ser
    20  21  22  23  24  25  26  27  28  29
                    Gly—Thr—Pro—NH₂
                    30  31  32
``` wherein Y is N(a) decanoyl and X is N(e) decanoyl.

38. The intranasal composition of claim 10 wherein said polypeptide is:

```
    H₂N—Ala—Ser—Asn—Leu—Ser—Thr—Ala—Gly—Leu—Gly—
          1               5                   10
    Lys—Leu—Ser—Gln—Glu—Leu—His—Lys—Gln—Thr—Tyr—
                         15                   20
    Pro—Arg—Thr—Asn—Thr—Gly—Ser—Gly—Thr—
                    25                   30
    Pro—(C=O)—NH₂.
```

39. The intranasal composition of claim 10 wherein said polypeptide is:

```
    CH₃—CH₂—(C=O)—Hn—
    Ala—Ser—Asn—Leu—Ser—Thr—Ala—Val—Leu—Gly—
      1               5                   10
    Lys—Leu—Ser—Gln—Glu—Leu—His—Lys—Gln—Thr—Tyr—
                         15                   20
    Pro—Arg—Thr—Asn—Thr—Gly—Ser—Gly—Thr—Pro—
                    25                   30
    (C=O)—NH₂.
```

* * * * *